United States Patent
Young et al.

(10) Patent No.: US 6,506,960 B1
(45) Date of Patent: Jan. 14, 2003

(54) ABSORBENT ARTICLE COMPRISING A LIQUID HANDLING MEMBER HAVING HIGH SUCTION AND HIGH PERMEABILITY

(75) Inventors: Gerald Alfred Young, Cincinnati, OH (US); Gary Dean Lavon, Oberursel (DE); Bruno Johannes Ehrnsperger, Frankfurt (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,225

(22) PCT Filed: Jun. 29, 1999

(86) PCT No.: PCT/US99/14632

§ 371 (c)(1),
(2), (4) Date: Dec. 20, 2000

(87) PCT Pub. No.: WO00/00118

PCT Pub. Date: Jan. 6, 2000

(30) Foreign Application Priority Data

Jun. 29, 1998 (WO) ................. PCT/US98/13449
Jun. 29, 1998 (WO) ................. PCT/US98/13497
Jun. 29, 1998 (WO) ................. PCT/US98/13521
Jun. 29, 1998 (WO) ................. PCT/US98/13523

(51) Int. Cl.$^7$ ............................................. A61F 13/15
(52) U.S. Cl. .................... 604/378; 604/369; 604/377
(58) Field of Search ............................. 604/369, 367, 604/377, 378

(56) References Cited

U.S. PATENT DOCUMENTS

| 6,013,589 A | 1/2000 | Desmarais et al. |
| 6,024,209 A | 2/2000 | Nolte |

FOREIGN PATENT DOCUMENTS

| EP | 0 512 010 B1 | 11/1992 |
| EP | 0 809 991 A1 | 12/1997 |
| WO | WO 98/05044 | 2/1998 |
| WO | WO 98/43580 | 10/1998 |

*Primary Examiner*—John J. Calvert
*Assistant Examiner*—Angela J Grayson
(74) *Attorney, Agent, or Firm*—Ian S. Robinson; Matthew P. Fitzpatrick; Ken K. Patel

(57) ABSTRACT

It is one aspect of the present invention to provide a liquid handling member which combines high liquid suction capability with a high permeability. It is another aspect of the present invention to provide liquid handling member which combines a high liquid suction capability with a fast 80 percent capacity absorption time. The present invention further provides devices for handling body liquids which comprise the liquid handling member of the present invention such as for example baby diapers, training pants, sanitary napkins, adult incontinence devices, bed mats, and the like.

10 Claims, 4 Drawing Sheets

ABSORBENT ARTICLE COMPRISING A LIQUID HANDLING MEMBER HAVING HIGH SUCTION AND HIGH PERMEABILITY

FIELD OF THE INVENTION

The present invention relates to devices for managing body fluids such as urine, sweat, saliva, blood, menses, purulence, or fecal material, and in particular to their ability to acquire and retain aqueous based materials. The invention further relates to disposable absorbent articles such as baby diapers or training pants, adult incontinence products, and feminine hygiene products and other body liquid handling articles such as catheters, urinals, and the like.

The invention further relates to devices for managing body liquids comprising a liquid handling member having high suction and high permeability.

BACKGROUND

Devices for managing body fluids are well known in the art and are frequently used for a wide variety of purposes. For example, the devices serve hygienic purposes such as diapers, sanitary napkins, adult incontinence products, underarm sweat pads, and the like. There is another class of such devices which serve medical purposes such as wound dressings or drainages, catheters, and the like. Accordingly such devices have been designed to cope with a large variety of different body liquids such as for example urine, sweat, saliva, blood, menses, purulence, fecal material, and the like.

The ability to provide better performing devices such as diapers has been contingent on the ability to develop relatively thin absorbent cores or structures that can acquire and store large quantities of discharged body fluids, in particular urine.

In addition, it is preferred to provide structures having a low capacity in the regions between the legs of the wearer such as in PCT application U.S. Ser. No. 97-05046, filed on Mar. 27, 1997, relating to the movement of fluid through certain regions of the article comprising materials having good acquisition and distribution properties to other regions comprising materials having specific liquid storage capabilities.

Most of the absorbent articles comprise therefore at least one fluid handling member that is designed for quickly acquiring and/or transporting liquid away from the loading point.

Examples of suitable liquid transport members based on crosslinked and curled cellulose are disclosed in European patent application No. 0 512 010 (Cook et al.). Further examples of suitable liquid transport members having high vertical liquid transport rates are disclosed in European patent application No. 0 809 991 (Schmidt et al.). Other suitable liquid transport members based on HIPE foams are disclosed in U.S. patent application Ser. No. 09-042418 (DesMarais et al., P&G case 7051).

Example structures comprising liquid transport members to transport liquid out of the crotch region are disclosed in PCT patent application WO 98/43580 (LaVon et al.).

Whilst such liquid transport members have been designed with capillary transport mechanisms in mind, thus aiming at positioning materials with smaller capillaries and/or increased hydrophilicity closer to the ultimate storage material, and materials with larger pores and less hydrophilicity closer to the loading zone, it has in addition been recognized, that acquisition/distribution materials have the tendency to not only transport the fluid, but also to retain the liquid, which can result under specific conditions to undesired effects, such as rewet or reduced fluid acquisition and/or distribution performance, which is particularly pronounced for acquisition/distribution materials being designed to balance acquisition and distribution properties.

Accordingly, liquid storage members have been developed, which have an improved balance of the fluid handling properties such that well performing acquisition/distribution materials or members can be dewatered efficiently by the storage materials or members. This is typically achieved by fluid storage materials or members having a high liquid suction capability.

In PCT patent application No. U.S. Ser. No. 98105044 (Palumbo et al.), absorbent structures are disclosed which comprise materials exhibiting a high liquid suction capability. These materials disclosed by the prior art employ small capillaries such as obtained by a small capillary HIPE foam, a mixture of superabsorber and high surface area fibers and the like to provide the high liquid suction capability. These structures have, however, the disadvantage that the small capillaries limit the liquid permeability thus providing large flow resistance and slow rate for liquid being absorbed.

Hence, it is an object of the present invention to provide a liquid handling member which overcomes the problems posed by the prior art.

It is a further object of the present invention to provide a liquid handling member which exhibits a high liquid suction capability in combination with a high liquid permeability and/or a high absorbent rate.

It is a further object of the present invention to provide a device for handling body liquids comprising a liquid handling member which exhibits a high liquid suction capability in combination with a high liquid permeability and/or a high absorbent rate.

SUMMARY OF THE INVENTION

The present invention provides a liquid handling member to be used in a device for handling by liquids.

The liquid handling member is characterized in that said liquid handling member has a capillary sorption absorption height at 50% of its capacity at 0 cm absorption height (CSAH50) according to the capillary sorption test of at least 50 cm and said liquid handling member further having a liquid permeability of at least 5 Darcy preferably at least 10 Darcy, most preferably at least 20 Darcy according to the saturated liquid permeability test.

Attentively, the liquid handling member is characterized in that said liquid handling member has a capillary sorption absorption height at 50% of its capacity at 0 cm absorption height (CSAH50) according to the capillary sorption test of at least 80 cm and said liquid handling member further having a liquid permeability of at least 2 Darcy according to the saturated liquid permeability test.

Yet alternatively, the liquid handling member is characterized in that said liquid handling member has a capillary sorption absorption height at 50% of its capacity at 0 cm absorption height (CSAH50) according to the capillary sorption test of at least 80 cm and said liquid handling member further having an absorption time to 80% of its capacity of less than 5 seconds according to the Demand Absorbency Test disclosed herein.

The liquid handling member preferably has a capillary sorption absorption capacity at 100 cm absorption height of at least 5 g/g, preferably at least 10 g/g.

The invention further relates to absorbent structures, comprising a first region for acquisition/distribution of fluid and a second region for storage of fluid. The first region comprises at least one member for acquiring and/or transporting liquid whereas the second region comprises said liquid handling members.

The present invention further provides a device for handling body liquids comprising a liquid handling member or an absorbent structure according to the present invention. The present invention further relates to absorbent articles such as baby diapers comprising a liquid handling member or an absorbent structure according to the present invention.

DETAILED DESCRIPTION OF THE INVENTION

Figure 1:
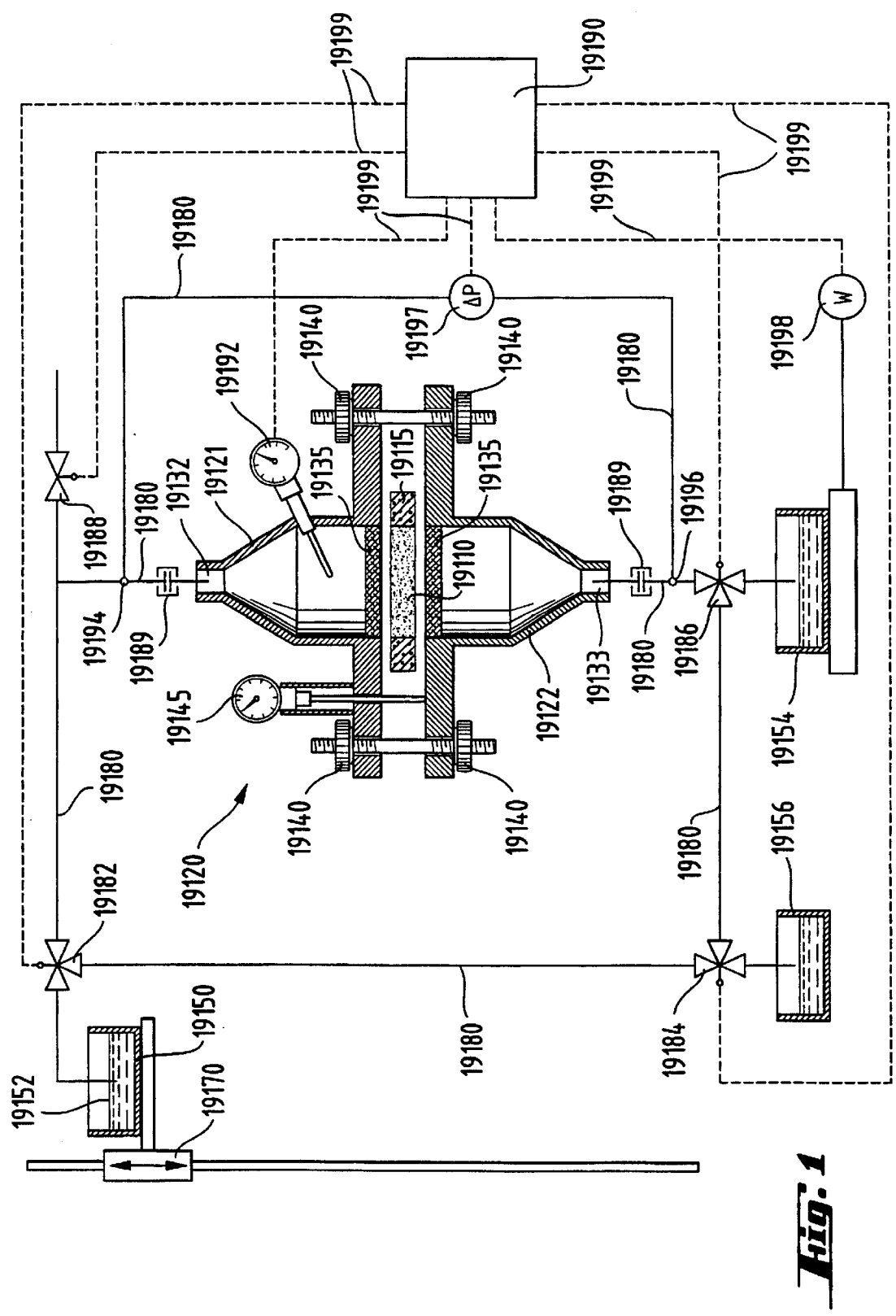
FIGS. 1, 2A and 2B show a schematic drawing of the setup for the liquid permeability test.

The present invention is described in the following by means of a variety of different embodiments and by means of a variety of different features. Further embodiments of the present invention may be obtained by combining features of one embodiment with features of another embodiment disclosed herein and/or with other features disclosed herein. These further embodiments are considered to be implicitly disclosed herein and hence form part of the present invention. It will be apparent to the skilled person that combinations of certain features may lead to non-functional articles not forming part of this present invention.

The present invention provides liquid handling members to be used in devices for handling body liquids. The present invention further provides devices for handling body liquids which comprise the liquid handling member of the present invention such as for example baby diapers, training pants, sanitary napkins, adult incontinence devices, bed mats, and the like.

The term "handling body liquid" includes but is not limited to acquiring, distributing, and storing body liquid.

It is one aspect of the present invention to provide a liquid handling member which combines high liquid suction capability with a high liquid permeability. In the context of the present invention, the term "liquid permeability" includes both in-plane and transplanar permeability. Saturated liquid permeability of a liquid handling member in the context of the present invention is defined in the saturated state, i.e. when the member has absorbed at least 90% of its capacity. It will be clear to the man skilled in the art that a high liquid permeability throughout the entire absorbent cycle is desired. In one embodiment of the present invention it is therefore preferred, that the liquid handling members exhibit high liquid permeability both in the saturated as well in the unsaturated state. The high liquid suction capability allows that well performing acquisition/distribution materials or members can be dewatered efficiently by the storage materials or members. A high liquid permeability in in-plane as well as transplanar direction allows efficient distribution of the acquired body liquids within the liquid handling member of the present invention, in particular distribution against gravity and relatively high flux rates.

For the purpose of this invention, trans-planar permeability is quantified by the permeability test defined hereinafter. It is recognized, however, that members having high in-plane permeability are also part of the scope of the present invention. The liquid handling member of the present invention has a permeability of at least 2 Darcy, preferably at least 5 Darcy, more preferably at least 10 Darcy, and most preferably a permeability of at least 20 Darcy.

It is another aspect of the present invention to provide liquid handling member which combines a high liquid suction capability with a fast absorption rate such as for example expressed by a fast absorption time to 80% capacity in the demand absorbency test. A fast 80 percent capacity absorption time is representative of the ability of liquid handling member to efficient be used the majority of its absorbent capacity in a fast and efficient way in order to avoid that the liquid storage becomes the rate limiting step for the performance of the device.

For the purpose of this invention, liquid suction is quantified by the capillary sorption test defined hereinafter. The liquid handling member of the present invention has a capillary Sorption Absorption Height at 50% of its capacity at 0 centimeter absorption height of at least 50 centimeter, preferably of at least 80 cm, more preferably of at least 100 cm.

For the purpose of this invention, the 80 percent capacity absorption time is quantified by the demand absorbency test defined hereinafter. The liquid handling member of the present invention has a 80 percent absorption time of less than 5 seconds, preferably a 80 percent absorption time of less than 2 second, more preferably of less than 1.5 seconds, most preferably of less than 1 second.

It is another aspect of the present invention to provide a liquid handling member having a capillary absorption capacity of at least 5 g/g, preferably at least 10 g/g at a high hydrostatic height of at least 50 cm, preferably at least 100 cm. A high absorbent capacity allows storage of larger quantities of body liquids such as for example urine gushes.

In the following, a suitable embodiment of the liquid handling member will be described. The liquid handling member is assembled from an inner material which is completely enveloped by a membrane. Suitable membrane materials are available from SEFAR of Ruischlikon, Switzerland, under the designation SEFAR 03-10/2 and under the designation SEFAR 03-5/1. A suitable foam material for use as inner material is available from Recticel of Brussels, Belgium, under the designation Bulpren S10 black. Other suitable inner materials may be obtained by punching holes of 2 mm diameter at a density of about 2 holes per square centimeter into materials available from Fisher Scientific of Germany, under the designation D&N Pelleus ball size 5 and under the designation D&N Pelleus ball size 7. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid handling member, it may also be required to choose similar materials with slightly different properties. After assembly, the liquid handling member is activated by immersing the liquid handling member in water or in synthetic urine until the liquid handling member is completely filled with liquid and until the membranes are completely wetted with liquid. After activation, a part of-the liquid inside the liquid handling member may be squeezed out by applying an external pressure to the liquid handling member. If the activation of the liquid handling member was successful, the liquid handling member should not suck air through the membranes.

Other liquid handling members suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications co-filed with the present application entitled "High flux liquid transport members comprising two different permeability regions" (P&G case CM1840MQ) filed in the name of Ehrnsperger et al., "Liquid transport member for high flux rates between two port regions" (P&G case CM1841MQ) filed in the name of Ehrnsperger et al., "Liquid transport member for high flux rates against gravity" (P&G case CM1842MQ) filed in the name of Ehmsperger et al., "Liquid transport member having high permeability bulk regions and high bubble point pressure port regions" (P&G case CM1843MQ) filed in the name of Ehrnsperger et al. All of these documents are enclosed herein by reference.

The particular geometry of the liquid handling member of the present invention can be varied according to the specific requirements off the intended application. If, for example, the liquid handling member is intended to be used in an absorbent article the liquid handling member may be defined such that its zone of intended liquid acquisition fits between the legs of the wearer and further that its intended liquid discharge zone matches the form of the storage member associated to it. Accordingly, the outer dimensions of the liquid handling member such as length, width, or thickness may also be adapted to the specific needs of the intended application. In this context, it has to be understood, however, that the design of the outer form of the liquid handling member may have an impact on its performance.

In one embodiment of the present invention, the liquid handling member of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules a according to NMR (nuclear magnetic resonance) spectroscopy methods well known in the art.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing its geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases a solid material and a gas or void phase and optionally a third liquid phase that may be partially or completely filling said void spaces. The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

It is another aspect of the present invention to provide an absorbent structure comprising a first region for acquisition/distribution of fluid and a second region for storage of fluid. The first region comprises at least one member for acquiring and/or transporting liquid such those well known in the art. The second region comprises a liquid handling member according to the present invention.

Device for Handling Body Liquid

It is one aspect of the present invention to provide a device for handling body liquids which comprises a liquid transport member according to the present invention and/or an absorbent structure according to the present invention. Such devices include but are not limited to disposable absorbent articles such as baby diapers or training pants, adult incontinence products, and feminine hygiene products and other body liquid handling articles such as catheters, urinals, and the like.

In one embodiment of the present invention, the device for handling body liquids is a disposable absorbent article such as a diaper, a training pant, a sanitary napkin, an adult incontinence device, or the like that comprises the liquid handling member of the present invention. Such an absorbent article may further comprise a liquid pervious topsheet, a liquid impervious backsheet at least partially peripherally joined to the topsheet. The absorbent article may further comprise a first liquid handling member which may serve as a acquisition and/or distribution member for the body liquid. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

Methods

Unless stated otherwise, all tests are carried out at about 32° C. +/−2° C. and at 35+/−15% relative humidity.

Unless stated otherwise, the synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Capillary Sorption Test

Purpose

The purpose of this test is to measure the capillary sorption absorbent capacity, as a function of height, of liquid handling members of the present invention. This test may also be used to measure the capillary sorption absorbent capacity of devices for handling body liquids according to the present invention. Capillary sorption is a fundamental property of any absorbent that governs how liquid is absorbed into the absorbent structure. In the Capillary Sorption experiment, capillary sorption absorbent capacity is measured as a function of fluid pressure due to the height of the sample relative to the test fluid reservoir.

The method for determining capillary sorption is well recognized. See Burgeni, A. A. and Kapur, C., "Capillary Sorption Equilibria in Fiber Masses," Textile Research Journal, 37 (1967), 356–366; Chatterjee, P. K., Absorbency, Textile Science and Technology 7, Chapter II, pp 29–84, Elsevier Science Publishers B. V, 1985; and U.S. Pat. No. 4,610,678, issued Sep. 9, 1986 to Weisman et al. for a discussion of the method for measuring capillary sorption of absorbent structures. The disclosure of each of these references is incorporated by reference herein.

Principle

A porous glass frit is connected via an uninterrupted column of fluid to a fluid reservoir on a balance. The sample is maintained under a constant confining weight during the experiment. As the porous structure absorbs fluid upon demand, the weight loss in the balance fluid reservoir is recorded as fluid uptake, adjusted for uptake of the glass frit as a function of height and evaporation. The uptake or capacity at various capillary suctions (hydrostatic tensions or heights) is measured. Incremental absorption occurs due to the incremental lowering of the frit (i.e., decreasing capillary suction).

Time is also monitored during the experiment to enable calculation of initial effective uptake rate (g/g/h) at a 200 cm height.

Reagents

Test Liquid: Synthetic urine is prepared by completely dissolving the following materials in distilled water.

| Compound | F.W. | Concentration (g/L) |
| --- | --- | --- |
| KCl | 74.6 | 2.0 |
| $Na_2SO_4$ | 142 | 2.0 |
| $(NH_4)H_2PO_4$ | 115 | 0.85 |
| $(NH_4)_2HPO_4$ | 132 | 0.15 |
| $CaCl_2.2H_2O$ | 147 | 0.25 |
| $MgCl_2.6H_2O$ | 203 | 0.5 |

General Description of Apparatus Set Up

The Capillary Sorption equipment, depicted generally as 520 in FIG. 3, used for this test is operated under TAPPI conditions (50% RH, 25° C.). A test sample is placed on a glass frit shown in FIG. 3 as 502 that is connected via a continuous column of test liquid (synthetic urine) to a balance liquid reservoir, shown as 506, containing test liquid. This reservoir 506 is placed on a balance 507 that is interfaced with a computer (not shown). The balance should be capable of reading to 0.001 g; such a balance is available from Mettler Toledo as PR1203 (Hightstown, N.J.). The glass frit 502 is placed on a vertical slide, shown generally in FIG. 3 as 501, to allow vertical movement of the test sample to expose the test sample to varying suction heights. The vertical slide may be a rodless actuator which is attached to a computer to record suction heights and corresponding times for measuring liquid uptake by the test sample. A preferred rodless actuator is available from Industrial Devices (Novato, Calif.) as item 202X4X34N-1D4B-84-P-C-S-E, which may be powered by motor drive ZETA 6104-83-135, available from CompuMotor (Rohnert, Calif.). Where data is measured and sent from actuator 501 and balance 507, capillary sorption absorbent capacity data may be readily generated for each test sample. Also, computer interface to actuator 501 may allow for controlled vertical movement of the glass frit 502. For example, the actuator may be directed to move the glass frit 502 vertically only after "equilibrium" (as defined below) is reached at each suction height.

The bottom of glass frit 502 is connected to Tygon® tubing 503 that connects the frit 505 to three-way drain stopcock 509. Drain stopcock 509 is connected to liquid reservoir 505 via glass tubing 504 and stopcock 510. (The stopcock 509 is open to the drain only during cleaning of the apparatus or air bubble removal.) Glass tubing 511 connects fluid reservoir 505 with balance fluid reservoir 506, via stopcock 510. Balance liquid reservoir 506 may consist of a lightweight 12 cm diameter glass dish 506A and cover 506B. The cover 506B has a hole through which glass tubing 511 contacts the liquid in the reservoir 506. The glass tubing 511 must not contact the cover 506B or an unstable balance reading will result and the test sample measurement cannot be used. In this context, it is to be understood that the volume of the liquid reservoir needs to be compatible with the absorbent capacity of the liquid handing member or the device to be tested. Hence, it may be necessary to choose a different liquid reservoir.

The glass frit diameter must be sufficient to accommodate the piston/cylinder apparatus, discussed below, for holding the test sample. The glass frit 502 is jacketed to allow for a constant temperature control from a heating bath. A suitable frit is a 350 ml fritted disc funnel specified as having 4 to 5.5 mm pores, available from Corning Glass Co. (Corning, N.Y.) as #36060-350F. The pores are fine enough to keep the frit surface wetted at capillary suction heights specified (the glass frit does not allow air to enter the continuous column of test liquid below the glass frit).

As indicated, the frit 502 is connected via tubing to fluid reservoir 505 or balance liquid reservoir 506, depending on the position of three-way stopcock 510.

Glass frit 502 is jacketed to accept water from a constant temperature bath. This will ensure that the temperature of the glass frit is kept at a constant temperature of 88° F. (31° C.) during the testing procedure. As is depicted in FIG. 3, the glass frit 502 is equipped with an inlet port 502A and outlet port 502B, which make a closed loop with a circulating heat bath shown generally as 508. (The glass jacketing is not depicted in FIG. 3. However, the water introduced to the jacketed glass frit 502 from bath 508 does not contact the test liquid and the test liquid is not circulated through the constant temperature bath. The water in the constant temperature bath circulates through the jacketed walls of the glass frit 502.)

Reservoir 506 and balance 507 are enclosed in a box to minimize evaporation of test liquid from the balance reservoir and to enhance balance stability during performance of the experiment. This box, shown generally as 512, has a top and walls, where the top has a hole through which tubing 511 is inserted.

Figure 2A:
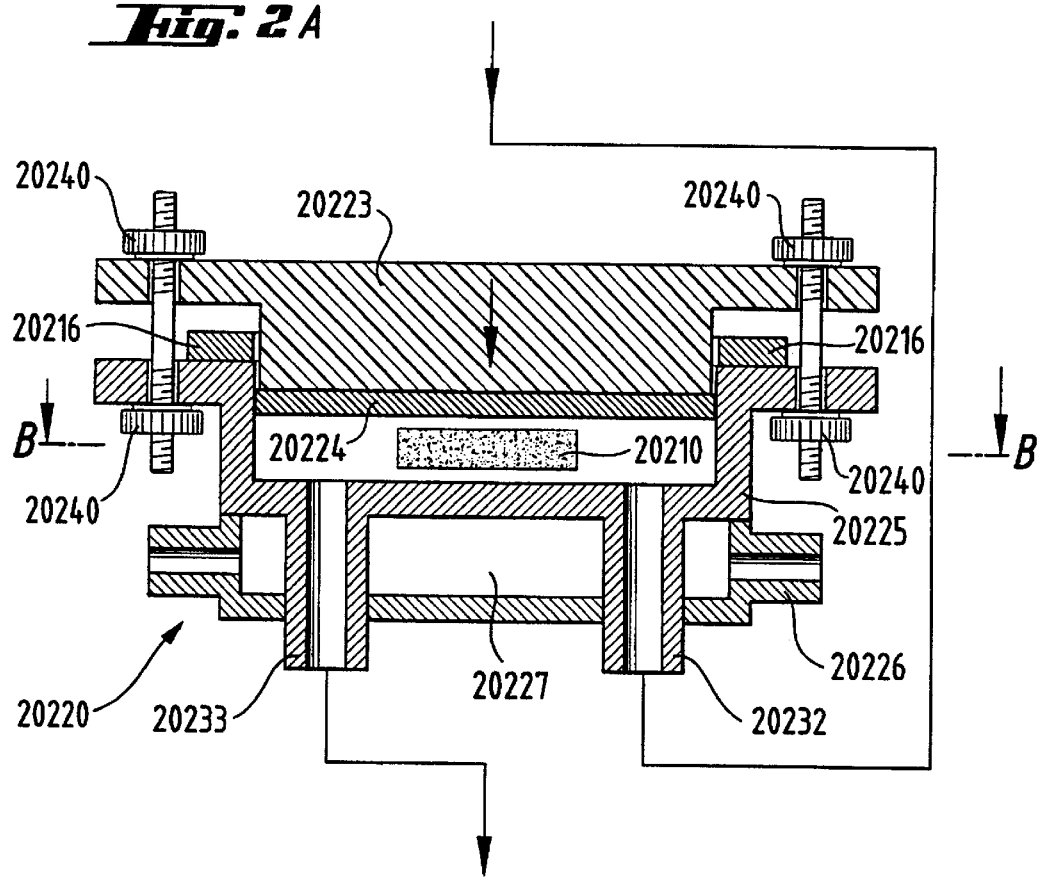
Figure 2B:
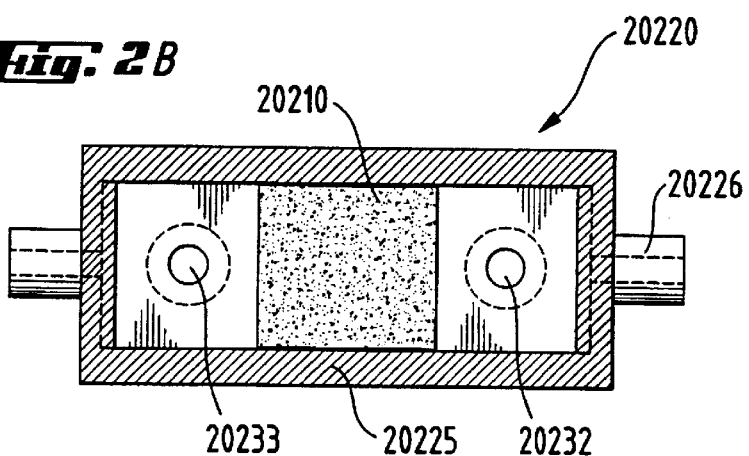
Figure 3A:
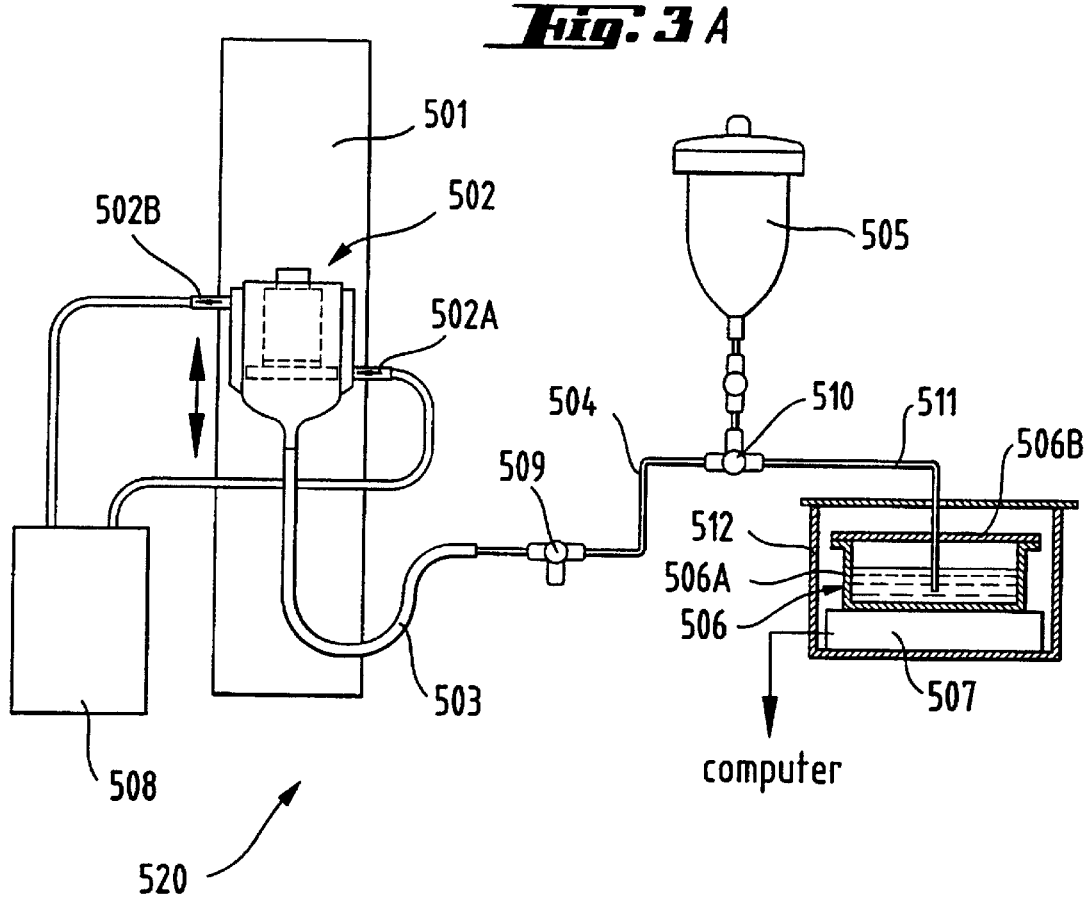
FIG. 3 shows a schematic drawing of the setup for the capillary sorption test.
Figure 3D:
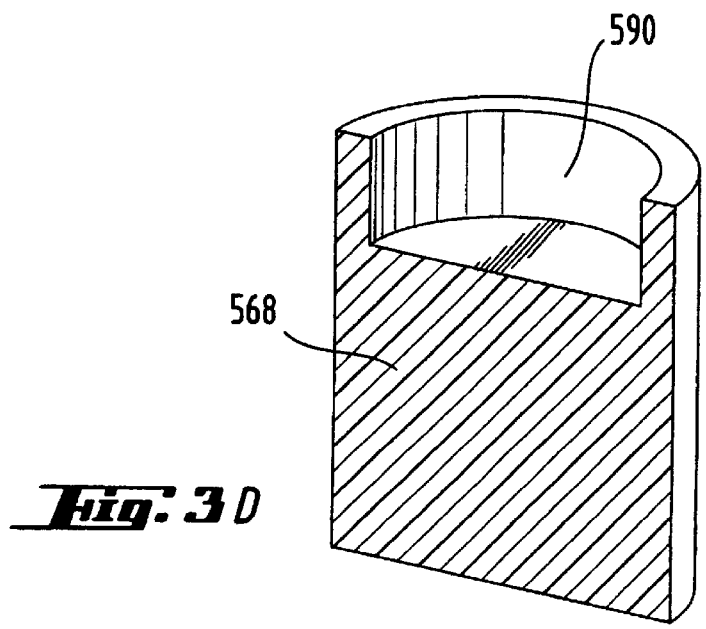
Figure 3B:
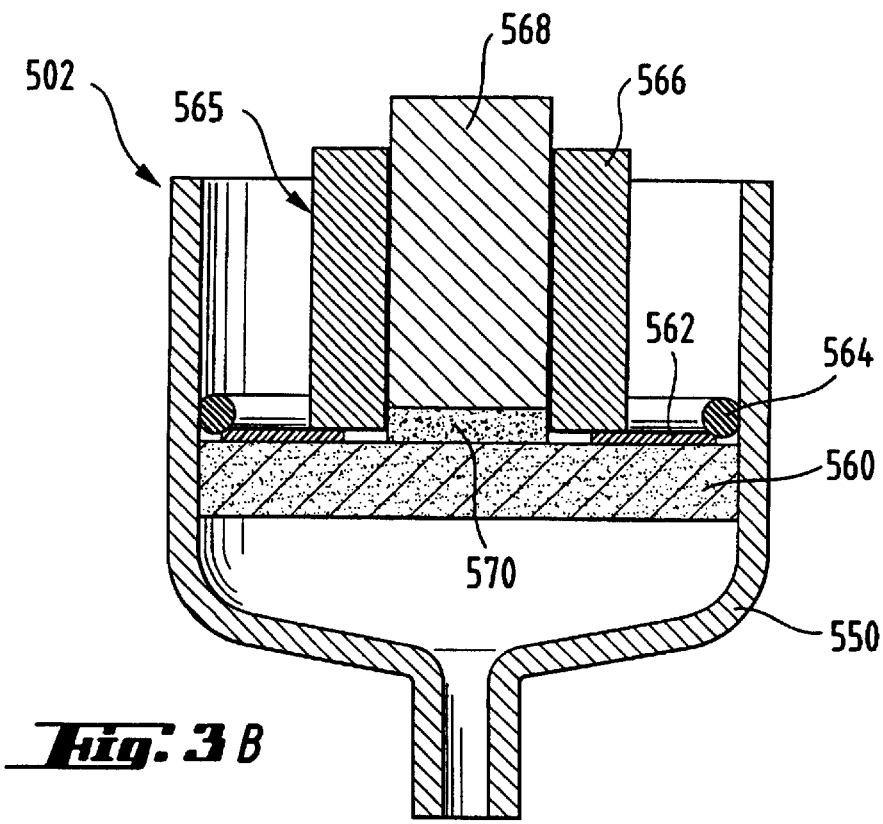
Figure 3C:
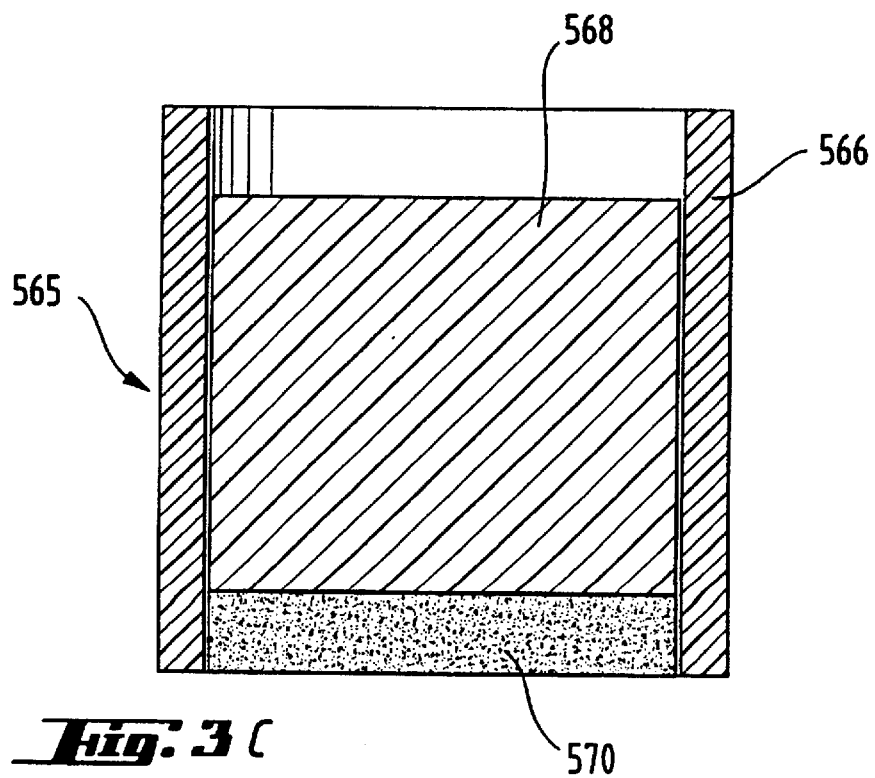

The glass frit 502 is shown in more detail in FIG. 2B. FIG. 2B is a cross-sectional view of the glass frit, shown without inlet port 502A and outlet port 502B. As indicated, the glass frit is a 350 ml fritted disc funnel having specified 4 to 5.5 mm pores. Referring to FIG. 2B, the glass frit 502 comprises a cylindrical jacketed funnel designated as 550 and a glass frit disc shown as 560. The glass frit 502 further comprises a cylinder/piston assembly shown generally as 565 (which comprises cylinder 566 and piston 568), which confines the test sample, shown as 570, and provides a small confining pressure to the test sample. To prevent excessive evaporation of test liquid from the glass frit disc 560, a Teflon ring shown as 562 is placed on top of the glass frit disc 560. The Teflon® ring 562 is 0.0127 cm thick (available as sheet stock from McMasterCarr as # 8569K16 and is cut to size) and is used to cover the frit disc surface outside of the cylinder 566, and thus minimizes evaporation from the glass frit. The ring outer diameter and inner diameter is 7.6 and 6.3 cm, respectively. The inner diameter of the Teflon® ring 562 is about 2 mm less than the outer diameter of cylinder 566. A Viton® O-ring (available from McMasterCarr as # AS568A-150 and AS56BA-151) 564 is placed on top of Teflon® ring 562 to seal the space between the inner wall of cylindrical jacketed funnel 550 and Teflon® ring 562, to further assist in prevention of evaporation. If the O-ring outer diameter exceeds the inner diameter of cylindrical jacketed funnel 550, the O-ring diameter is reduced to fit the funnel as follows: the O-ring is cut open, the necessary amount of O-ring material is cut off, and the O-ring is glued back together such that the O-ring contacts the inner wall of the cylindrical jacketed funnel 550 all around its periphery. While the above described frit represents one suitable example of frit, it may be necessary to use of frit having dimensions different from the above dimensions in order to better fit the dimensions of the liquid handling member or the device to be tested. The surface area of the frit should resemble as closely as possible the surface area of the acquisition zone of the liquid handling member or the device in order to fully use the acquisition zone and in order to minimize the evaporation from the frit.

As indicated, a cylinder/piston assembly shown generally in FIG. 2B as 565 confines the test sample and provides a small confining pressure to the test sample 570. Referring to FIG. 2C, assembly 565 consists of a cylinder 566, a cup-like Teflon® piston indicated by 568 and, when necessary, a weight or weights (not shown) that fits inside piston 568. (Optional weight will be used when necessary to adjust the combined weight of the piston and the optional weight so a confining pressure of 0.2 psi is attained depending on the test sample's dry diameter. This is discussed below.) The cylinder 566 is Lexan® bar stock and has the following dimensions: an outer diameter of 7.0 cm diameter of 6.0 cm and a height of 6.0 cm. The Teflon® piston 568 has the following dimensions: an outer diameter that is 0.02 cm less than the inner diameter of cylinder 566. As shown in FIG. 2D, the end of the piston 568 that does not contact the test sample is bored to provide a 5.0 cm diameter by about 1.8 cm deep chamber 590 to receive optional weights (dictated by the test sample's actual dry diameter) required to attain a test sample confining pressure of 0.2 psi (1.4 kPa). In other words, the total weight of the piston 568 and any optional weights (not shown in figures) divided by the test sample's actual diameter (when dry) should be such that a confining pressure of 0.2 psi is attained. Cylinder 566 and piston 568 (and optional weights) are equilibrated at 31° C. for at least 30 minutes prior to conducting the capillary sorption absorbent capacity measurement. Again, the above described dimensions are chosen to fit the above described exemplary frit. Of course, when a different frit is chosen the dimensions of the cylinder/piston assembly need to be adjusted accordingly.

A non-surfactant treated or incorporated apertured film (14 cm×14 cm ) (not shown) is used to cover the glass frit 502 during Capillary Sorption experiments to minimize air destablization around the sample. Apertures are large enough to prevent condensation from forming on the underside of the film during the experiment.

Test Sample Preparation

For the present procedure, it is important, that the dimensions of the sample and of the frit should not be too different. To achieve this, two approaches can be taken:
  a) For test samples, which can be readily adjusted to a suitable size, such as by cutting these, both the size of this cutting as well as of the frit are chosen to be a circular shaped structure of 5.4 cm diameter, such as can be done by using a conventional arc punch.
  b) When the test sample cannot readily be cut to this dimension, the size and preferably also the shape of the frit has to be adjusted to the size and shape of the test sample.

In both cases, the test sample can be a readily separable element of a member or a device, it can be a particular component of any of these, or can be a combination of components thereof. It might also be necessary to adjust the size of the liquid reservoir to match the varying requirements.

The dry weight of the test sample (used below to calculate capillary sorption absorbent capacity) is the weight of the test sample prepared as above under ambient conditions.

Experimental Set Up

1. Place a clean, dry glass frit 502 in a funnel holder attached to the vertical slide 501. Move the funnel holder of the vertical slide such that the glass frit is at the 0 cm height.
2. Set up the apparatus components as shown in FIG. 3, as discussed above.
3. Place 12 cm diameter balance liquid reservoir 506 on the balance 507. Place plastic lid 506B over this balance liquid reservoir 506 and a plastic lid over the balance box 512 each with small holes to allow the glass tubing 511 to fit through. Do not allow the glass tubing to touch the lid 506B of the balance liquid reservoir or an unstable balance reading will result and the measurement cannot be used.
4. Stopcock 510 is closed to tubing 504 and opened to glass tubing 511. Fluid reservoir 505, previously filled with test fluid, is opened to allow test fluid to enter tubing 511, to fill balance fluid reservoir 506.
5. The glass frit 502 is leveled and secured in place. Also, ensure that the glass frit is dry.
6. Attach the Tygon® tubing 503 to stopcock 509. (The tubing should be long enough to reach the glass frit 502 at its highest point of 200 cm with no kinks.) Fill this Tygon® tubing with test liquid from liquid reservoir 505.
7. Attach the Tygon® tubing 503 to the level glass frit 502 and then open stopcock 509 and stopcock 510 leading from fluid reservoir 505 to the glass frit 502. (Stopcock 510 should be closed to glass tubing 511.) The test liquid fills the glass frit 502 and removes all trapped air during filling of the level glass frit. Continue to fill until the fluid level exceeds the top of the glass frit disc 560. Empty the funnel and remove all air bubbles in the tubing and inside the funnel. Air bubbles may be removed by inverting glass frit 502 and allowing air bubbles to rise and escape through the drain of stopcock 509. (Air bubbles typically collect on the bottom of the glass frit disc 560.) Relevel the frit using a small enough level that it will fit inside the jacketed funnel 550 and onto the surface of glass frit disc 560.
8. Zero the glass frit with the balance liquid reservoir 506. To do this, take a piece of Tygon® tubing of sufficient length and fill it with the test liquid. Place one end in the balance liquid reservoir 506 and use the other end to position the glass frit 502. The test liquid level indicated by the tubing (which is equivalent to the balance liquid reservoir level) is 10 mm below the top of the glass frit disc 560. If this is not the case, either adjust the amount of liquid in the reservoir or reset the zero position on the vertical slide 501.
9. Attach the outlet and inlet ports from the temperature bath 508 via tubing to the inlet and outlet ports 502A and 502B, respectively, of the glass frit. Allow the temperature of the glass frit disc 560 to come to 31° C. This can be measured by partially filling the glass frit with test liquid and measuring its temperature after it has reached equilibrium temperature. The bath will need to be set a bit higher than 31° C. to allow for the dissipation of heat during the travel of water from the bath to the glass frit.

10. The glass frit is equilibrated for 30 minutes.

Capillary Somtion Parameters

The following describes a computer program that will determine how long the glass frit remains at each height.

In the capillary sorption software program, a test sample is at some specified height from the reservoir of fluid. As indicated above, the fluid reservoir is on a balance, such that a computer can read the balance at the end of a known time interval and calculate the flow rate (Delta reading/time interval) between the test sample and reservoir. For purposes of this method, the test sample is considered to be at equilibrium when the flow rate is less than a specified flow rate for a specified number of consecutive time intervals. It is recognized, that for certain material, actual equilibrium may not be reached when the specified "EQUILIBRIUM CONSTANT" is reached. The time interval between readings is 5 seconds.

The number of readings in the delta table is specified in the capillary sorption menu as "EQUILIBRIUM SAMPLES". The maximum number of deltas is 500. The flow rate constant is specified in the capillary sorption menu as "EQUILIBRIUM CONSTANT".

The Equilibrium Constant is entered in units of grams/sec, ranging from 0.0001 to 100.000.

The following is a simplified example of the logic. The table shows the balance reading and Delta Flow calculated for each Time Interval.

Equilibrium Samples=3

| | Equilibrium Constant = 0.0015 | |
|---|---|---|
| Time Interval | Balance Value (g) | Delta Flow (g/sec) |
| 0 | 0 | |
| 1 | 0.090 | 0.0180 |
| 2 | 0.165 | 0.0150 |
| 3 | 0.225 | 0.0120 |
| 4 | 0.270 | 0.0090 |
| 5 | 0.295 | 0.0050 |
| 6 | 0.305 | 0.0020 |
| 7 | 0.312 | 0.0014 |
| 8 | 0.316 | 0.0008 |
| 9 | 0.318 | 0.0004 |

DELTA TABLE

| Time | 0 | 1 | 2 | 3 | 4 | 5 | 6 | 7 | 8 | 9 |
|---|---|---|---|---|---|---|---|---|---|---|
| Delta 1 | 9999 | 0.0180 | 0.0180 | 0.0180 | 0.0090 | 0.0090 | 0.0090 | 0.0014 | 0.0014 | 0.0014 |
| Delta 2 | 9999 | 9999 | 0.0150 | 0.0150 | 0.0150 | 0.0050 | 0.0050 | 0.0050 | 0.0008 | 0.0008 |
| Delta 3 | 9999 | 9999 | 9999 | 0.0120 | 0.0120 | 0.0120 | 0.0020 | 0.0020 | 0.0020 | 0.0004 |

The equilibrium uptake for the above simplified example is 0.318 gram.

The following is the code in C language used to determine equilibrium uptake:

```
/*     takedata.c    */
int take_data(int equil_samples,double equilibrium_constant)
{
double delta;
static double deltas[500];          /* table to store up to 500
                                       deltas */
double value;
double prev_value;
clock_t next_time;
int i;
for (i=0; i<equil_samples; i++)
deltas[i] = 9999.;                  /* initialize all values in the
                                       delta table to 9999. gms/sec */
delta_table_index = 0;              /* initialize where in the table
                                       to store the next delta */
equilibrium_reached = 0;            /* initialize flag to indicate
                                       equilibrium has not been
                                       reached */
next_time = clock();                /* initialize when to take the
                                       next reading */
prev_reading = 0.;                  /* initialize the value of the
                                       previous reading from the
                                       balance */
while (!equilibrium_reached) {      /* start of loop for checking
                                       for equilibrium */
next_time += 5000L;                 /* calculate when to take next
                                       reading */
while (clock() < next_time);        /* wait until 5 seconds has
                                       elapsed from prev reading */
value = get_balance__reading();     /* read the balance in
                                       grams */
delta = fabs(prev_value - value) /5.0;  /* calculate absolute value of
                                       flow in last 5 seconds */
prev_value = value;                 /* store current value for
                                       next loop */
deltas[delta_table_index] = delta;  */ store current delta value
                                       in the table of deltas */
delta_table_index++;                /* increment pointer to next
                                       position in table */
if (delta_table_index == equil_samples) /* when the number of
                                       deltas = the number of */
delta_table_index = 0;              /* equilibrium samples
                                       /* specified, reset the */
                                       /* pointer to the start of */
                                       /* the table. This way the */
                                       /* table always contains the */
                                       /* last xx current samples. */
equilibrium_reached = 1;            /* set the flag to indicate
                                       equilibrium is reached */
for (i=0; i<equil_samples; i++)     /* check all the values in the
                                       delta table */
if (deltas[i] >= equilibrium_constant)  /* if any value is > or = to
                                       the equilibrium constant */
equilibrium_reached = 0;            /* set the equilibrium flag to 0
                                       (not at equilibrium) */
}                                   /* go back to the start of
                                       the loop */
}
```

Capillary Sorption Parameters
Load Description (Confining Pressure): 0.2 psi load
Equilibrium Samples (n): 50
Equilibrium Constant: 0.0005 g/sec
Setup Height Value: 100 cm
Finish Height Value: 0 cm Hydrostatic Head Parameters: 200, 180, 160, 140, 120, 100, 90, 80, 70, 60, 50, 45, 40, 35, 30, 25, 20, 15, 10, 5 and 0 cm.

The capillary sorption procedure is conducted using all the heights specified above, in the order stated, for the measurement of capillary sorption absorbent capacity. Even if it is desired to determine capillary sorption absorbent capacity at a particular height (e.g., 35 cm ), the entire series of hydrostatic head parameters must be completed in the order specified. Although all these heights are used in performance of the capillary sorption test to generate capillary sorption isotherms for a test sample, the present disclosure describes the storage absorbent members in terms of their absorbent properties at specified heights of 200, 140, 100, 50, 35 and 0 cm.

Caipillary Sormtion Procedure

1) Follow the experimental setup procedure.
2) Make sure the temperature bath 508 is on and water is circulating through the glass frit 502 and that the glass frit disc 560 temperature is 31° C.
3) Position glass frit 502 at 200 cm suction height. Open stopcocks 509 and 510 to connect glass frit 502 with the balance liquid reservoir 506. (Stopcock 510 is closed to liquid reservoir 505.) Glass frit 502 is equilibrated for 30 minutes.
4) Input the above capillary sorption parameters into the computer.
5) Close stopcocks 509 and 510.
6) Move glass frit 502 to the set up height, 100 cm.
7) Place Teflon® ring 562 on surface of glass frit disc 560. Put O-ring 564 on Teflon® ring. Place pre-heated cylinder 566 concentrically on the Teflon® ring. Place test sample 570 concentrically in cylinder 566 on glass frit disc 560. Place piston 568 into cylinder 566. Additional confining weights are placed into piston chamber 590, if required.
8) Cover the glass frit 502 with apertured film.
9) The balance reading at this point establishes the zero or tare reading.
10) Move the glass frit 502 to 200 cm.
11) Open stopcocks 509 and 510 (stopcock 510 is closed to fluid reservoir 505) and begin balance and time readings.

Glass Frit Correction (blank correct uptake)

Since the glass frit disc 560 is a porous structure, the glass frit (502) capillary sorption absorption uptake (blank correct uptake) must be determined and subtracted to get the true test sample capillary sorption absorption uptake. The glass frit correction is performed for each new glass frit used. Run the capillary sorption procedure as described above, except without test sample, to obtain the Blank Uptake (g). The elapsed time at each specified height equals the Blank Time (s).

Evaporation Loss Correction

1) Move the glass frit 502 to 2 cm above zero and let it equilibrate at this height for 30 minutes with open stopcocks 509 and 510 (closed to reservoir 505).
2) Close stopcocks 509 and 510.
3) Place Teflon® ring 562 on surface of glass frit disc 560. Put O-ring 564 on Teflon® ring. Place pre-heated cylinder 566 concentrically on the Teflon® ring. Place piston 568 into cylinder 586. Place apertured film on glass frit 502.
4) Open stopcocks 509 and 510 (closed to reservoir 505) and record balance reading and time for 3.5 hours. Calculate Sample Evaporation (g/hr) as follows:
   [balance reading at 1 hr—balance reading at 3.5 hr] 12.5 hr.

Even after taking all the above precautions, some evaporative loss will occur, typically around 0.10 gm/hr for both the test sample and the frit correction. Ideally, the sample evaporation is measured for each newly installed glass frit 502.

Cleaning the Equipment New Tygonõ tubing 503 is used when a glass frit 502 is newly installed. Glass tubing 504 and 511, fluid reservoir 505, and balance liquid reservoir 506 are cleaned with 50% Clorox Bleach® in distilled water, followed by distilled water rinse, if microbial contamination is visible.

a. Cleaning After Each Experiment

At the end of each experiment (after the test sample has been removed), the glass frit is forward flushed (i.e., test liquid is introduced into the bottom of the glass frit) with 250 ml test liquid from liquid reservoir 505 to remove residual test sample from the glass frit disc pores. With stopcocks 509 and 510 open to liquid reservoir 505 and closed to balance liquid reservoir 506, the glass frit is removed from its holder, turned upside down and is rinsed out first with test liquid, followed by rinses with acetone and test liquid (synthetic urine). During rinsing, the glass frit must be tilted upside down and rinse fluid is squirted onto the test sample contacting surface of the glass frit disc. After rinsing, the glass frit is forward flushed a second time with 250 ml test liquid (synthetic urine). Finally, the glass frit is reinstalled in its holder and the frit surface is leveled.

b. Monitoring Glass Frit Performance

Glass frit performance must be monitored after each cleaning procedure and for each newly installed glass frit, with the glass frit set up at 0 cm position. 50 ml of test liquid are poured onto the leveled glass frit disc surface (without Teflon® ring, O-ring and the cylinder/piston components). The time it takes for the test fluid level to drop to 5 mm above the glass frit disc surface is recorded. A periodic cleaning must be performed if this time exceeds 4.5 minutes.

c. Periodic Cleaning

Periodically, (see monitoring frit performance, above) the glass frits are cleaned thoroughly to prevent clogging. Rinsing fluids are distilled water, acetone, 50% Clorox Bleach® in distilled water (to remove bacterial growth) and test liquid. Cleaning involves removing the glass frit from the holder and disconnecting all tubing. The glass frit is forward flushed (i.e., rinse liquid is introduced into the bottom of the glass frit) with the frit upside down with the appropriate fluids and amounts in the following order:

1. 250 ml distilled water.
2. 100 ml acetone.
3. 250 ml distilled water.
4. 100 ml 50:50 Clorox®/distilled water solution.
5. 250 ml distilled water.
6. 250 ml test fluid.

The cleaning procedure is satisfactory when glass frit performance is within the set criteria of fluid flow (see above) and when no residue is observable on the glass frit disc surface. If cleaning can not be performed successfully, the frit must be replaced.

Calculations

The computer is set up to provide a report consisting of the capillary suction height in cm, time, and the uptake in grams at each specified height. From this data, the capillary suction absorbent capacity, which is corrected for both the frit uptake and the evaporation loss, can be calculated. Also, based on the capillary suction absorbent capacity at 0 cm , the capillary absorption efficiency can be calculated at the specified heights. In addition, the initial effective uptake rate at 200 cm is calculated.

Blank Correct Uptake $$\text{Blank Correct Uptake (g)} = \text{Blank Uptake (g)} - \frac{\text{Blank Time (s)} * \text{Blank Evap. (g/hr)}}{3600 \text{ (s/hr)}}$$

Capillary Suction Absorbent Capacity ("CSAC")

$$\text{Net Uptake (g/g)} = \frac{\text{Sample Uptake (g)} - \frac{\text{Sample Time (s)} * \text{Sample Evap. (g/hr)}}{3600 \text{ s/hr}} - \text{Blank Correct Uptake (g)}}{\text{Dry Weight of Sample (g)}}$$

Initial Effective Uptake Rate at 200 cm ("IEUR")
IEUR (g/g/hr)=CSAC at 200 cm (g/g)
  Sample Time at 200 cm (s)
Reporting A minimum of two measurements should be taken for each sample and the uptake averaged at each height to calculate Capillary Sorption Absorbent Capacity (CSAC) for a given absorbent member or a given high surface area material.

With these data, the respective values can be calculated:

The Capillary Sorption Desorption Height at which the material has released x% of its capacity at 0 cm (i.e. of CSAC 0), (CSDH x) expressed in cm;

The Capillary Sorption Absorption Height at which the material has absorbed y% of its capacity at 0 cm (i.e. of CSAC 0), (CSAH y) expressed in cm;

The Capillary Sorption Absorbent Capacity at a certain height z (CSAC z) expressed in units of g {of fluid}/g { of material}; especially at the height zero (CSAC 0), and at heights of 35 cm , 40 cm , etc The Capillary Sorption Absorption Efficiency at a certain height z (CSAE z) expressed in %, which is the ratio of the values for CSAC 0 and CSAC z.

If two materials are combined (such as the first being used as acquisition/distribution material, and the second being used as liquid storage material), the CSAC value (and hence the respective CSAE value) of the second material can be determined for the CSDH x value of the first material.

Demand Absorbency Test

The demand absorbency test is intended to measure the liquid capacity of liquid handling member and to measure the absorption speed of liquid handling member against zero hydrostatic pressure. The test may also be carried out for devices for managing body liquids containing a liquid handling member.

The apparatus used to conduct this test consists of a square basket of a sufficient size to hold the liquid handling member suspended on a frame. At least the lower plane of the square basket consists of an open mesh that allows liquid penetration into the basket without substantial flow resistance for the liquid uptake. For example, an open wire mesh made of stainless steel having an open area of at least 70 percent and having a wire diameter of 1 mm, and an open mesh size of at about 6 mm is suitable for the setup of the present test. In addition, the open mesh should exhibit sufficient stability such that it substantially does not deform under load of the test specimen when the test specimen is filled up to its full capacity.

Below the basket, a liquid reservoir is provided. The height of the basket can be adjusted so that a test specimen which is placed inside the basket may be brought into contact with the surface of the liquid in the liquid reservoir. The liquid reservoir is placed on the electronic-balance connected to a computer to read out the weight of the liquid about every 0.01 sec during the measurement. The dimensions of the apparatus are chosen such that the liquid handling member to be tested fits into the basket and such that the intended liquid acquisition zone of the liquid handing member is in contact with the lower plane of the basket.

The dimensions of the liquid reservoir are chosen such that the level of the liquid surface in the reservoir does not substantially change during the measurement. A typical reservoir useful for testing liquid handling members has a size of at least 320 mm×370 mm and can hold at least about 4500 g of liquid.

Before the test, the liquid reservoir is filled with synthetic urine. The amount of synthetic urine and the size of the liquid reservoir should be sufficient such that the liquid level in the liquid reservoir does not change when the liquid capacity of the liquid handling member to be tested is removed from the reservoir.

The temperature of the liquid and the environment for the test should reflect in-use conditions of the member. Typical temperature for use in baby diapers are 32 degrees Celsius for the environment and 37 degrees Celsius for the synthetic urine. The test may be done at room temperature if the member tested has no significant dependence of its absorbent properties on temperature.

The test is setup by lowering the empty basket until the mesh is just completely immersed in the synthetic urine in the reservoir. The basket is then raised again by about 0.5 to 1 mm in order to establish an almost zero hydrostatic suction, care should be taken that the liquid stays in contact with the mesh. If necessary, the mesh needs to be brought back into contact with the liquid and zero level be readjusted.

The test is started by:
1. starting the measurement of the electronic balance;
2. placing the liquid handling member on the mesh such that the acquisition zone of the member is in contact with the liquid;
3. immediately adding a low weigh on top of the member in order to provide a pressure of 165 Pa for better contact of the member to the mesh.

During the test, the liquid uptake by the liquid handling member is recorded by measuring the weight decrease of the liquid in the liquid reservoir. The test is stopped after 30 minutes.

At the end of the test, the total liquid uptake of the liquid handling member is recorded. In addition, the time after which the liquid handling member had absorbed 80 percent of its total liquid uptake is recorded. The zero time is defined as the time where the absorption of the member starts. The initial absorption speed of the liquid handling member is from the initial linear slope of the weight vs. time measurement curve.

Saturated Liquid Permeability Test

In order to measure the saturated liquid permeability, the liquid permeability test as described below is executed with the test sample being at 100% saturation. Saturation in this context is defined as the test sample having absorbed 100% of its capacity that it has in the demand absorbency test.

Generally, the test can be carried out with a suitable test fluid representing the transport fluid, such as with Jayco SynUrine as available from Jayco Pharmaceuticals Company of Camp Hill, Pa., and can be operated-under controlled laboratory conditions of about 23 +/−2° C. and at 50+/−10% relative humidity. However, when using polymeric foam materials, such as disclosed in U.S. Pat. No. 5,563,179 or U.S. Pat. No. 5,387,207, it has been found more useful to operate the test at an elevated temperature of 31° C., and by using de-ionized water as test fluid.

In principle, this tests is based on Darcy's law, according to which the volumetric flow rate of a liquid through any porous medium is proportional to the pressure gradient, with the proportionality constant related to permeability.

$$Q/A = (k/\eta) * (\Delta P/L)$$

where:

Q=Volumetric Flow Rate [cm$^3$/s];
A=Cross Sectional Area [cm$^2$];
k=Permeability (cm$^2$) (with 1 Darcy corresponding to 9.869* 10$^{-13}$ m$^2$);
η=Viscosity (Poise) [Pa*s];
ΔP/L=Pressure Gradient [Pa/m];
L=caliper of sample [cm].

Hence, permeability can be calculated—for a fixed or given sample cross-sectional area and test liquid viscosity—by measurement of pressure drop and the volumetric flow rate through the sample:

$$k = (Q/A) * (L/\Delta P) * \eta$$

The test can be executed in two modifications, the first referring to the transplanar permeability (i.e. the direction of flow is essentially along the thickness dimension of the material), the second being the in-plane permeability (i.e. the direction of flow being in the x-y-direction of the material).

The test set-up for the transplanar permeability test can be see in FIG. 1 which is a schematic diagram of the overall equipment and—as an insert diagram—a partly exploded cross-sectional, not to scale view of the sample cell.

The test set-up comprises a generally circular or cylindrical sample cell (19120), having an upper (19121) and lower (19122) part. The distance of these parts can be measured and hence adjusted by means of each three circumferentially arranged caliper gauges (19145) and adjustment screws (19140). Further, the equipment comprises several fluid reservoirs (19150, 19154, 19156) including a height adjustment (19170) for the inlet reservoir (19150) as well as tubings (19180), quick release fittings (19189) for connecting the sample cell with the rest of the equipment, further valves (19182, 19184, 19186, 19188). The differential pressure transducer (19197) is connected via tubing (19180) to the upper pressure detection point (19194) and to the lower pressure detection point (19196). A Computer device (19190) for control of valves is further connected via connections (19199) to differential pressure transducer (19197), temperature probe (19192), and weight scale load cell (19198).

The circular sample (19110) having a diameter of 1 in (about 2.54 cm ) is placed in between two porous screens (19135) inside the sample cell (19120), which is made of two 1 in (2.54 cm ) inner diameter cylindrical pieces (19121, 19122) attached via the inlet connection (19132) to the inlet reservoir (19150) and via the outlet connection (19133) to the outlet reservoir (19154) by flexible tubing (19180), such as tygon tubing. Closed cell foam gaskets (19115) provide leakage protection around the sides of the sample. The test sample (19110) is compressed to the caliper corresponding to the desired wet compression, which is set to 0.2 psi (about 1.4 kPa) unless otherwise mentioned. Liquid is allowed to flow through the sample (19110) to achieve steady state flow. Once steady state flow through the sample (19110) has been established, volumetric flow rate and pressure drop are recorded as a function of time using a load cell (19198) and the differential pressure transducer (19197). The experiment can be performed at any pressure head up to 80 cm water (about 7.8 kPa), which can be adjusted by the height adjusting device (19170). From these measurements, the flow rate at different pressures for the sample can be determined.

The equipment is commercially available as a liquid Permeameter such as supplied by Porous Materials, Inc, Ithaca, N.Y. US under the designation PMI Liquid Permeameter, such as further described in respective user manual of 2/97, and modified according to the present description. This equipment includes two Stainless Steel Frits as porous screens (19135), also specified in said brochure. The equipment consists of the sample cell (19120), inlet reservoir (19150), outlet reservoir (19154), and waste reservoir (19156) and respective filling and emptying valves and connections, an electronic scale, and a computerized monitoring and valve control unit (19190).

The gasket material (19115) is a Closed Cell Neoprene Sponge SNC-1 (Soft), such as supplied by Netherland Rubber Company, Cincinnati, Ohio, US. A set of materials with varying thickness in steps of 1/16" (about 0.159 cm) should be available to cover the range from 1/16"–1/2" (about 0.159 cm to about 1.27 cm ) thickness.

Further a pressurized air supply is required, of at least 60 psi (4.1 bar), to operate the respective valves.

The test is then executed by the following steps:
1) Preparation of the test sample(s):

In a preparatory test, it is determined, if one or more members of the present invention are required, wherein the test as outlined below is run at the lowest and highest pressure. The number of members is then adjusted so as to maintain the flow rate during the test between 0.5 cm$^3$/seconds at the lowest pressure drop and 15 cm $^3$/second at the highest pressure drop. The flow rate for the sample should be less than the flow rate for the blank at the same pressure drop. If the sample flow rate exceeds that of the blank for a given pressure drop, more layers should be added to decrease the flow rate. Sample size: Samples are cut to 1" (about 2.54 cm ) diameter, by using an arch punch, such as supplied by McMaster-Carr Supply Company, Cleveland, Ohio, US. If samples have too little internal strength or integrity to maintain their structure during the required manipulation, a conventional low basis weight support means can be added, such as a PET scrim or net.

Thus, at least two samples (made of the required number of layers each, if necessary) are precut. Then, one of these is saturated in deionized water at the temperature the experiment is to be performed (70° F., (31° C.) unless otherwise noted).

The caliper of the wet sample is measured (if necessary after a stabilization time of 30 seconds) under the desired compression pressure for which the experiment will be run by using a conventional caliper gauge (such as supplied by AMES, Waltham, Mass., US) having a pressure foot diameter of 1 1/8 (about 2.86 cm ), exerting a pressure of 0.2 psi (about 1.4 kPa) on the sample (19110), unless otherwise desired.

An appropriate combination of gasket materials is chosen, such that the total thickness of the gasketing foam (19115) is between 150 and 200% of the thickness of the wet sample (note that a combination of varying thicknesses of gasket material may be needed to achieve the overall desired thickness). The gasket material (19115) is cut to a circular size of 3" in diameter, and a 1 inch (2.54 cm) hole is cut into the center by using the arch punch.

In case, that the sample dimensions change upon wetting, the sample should be cut such that the required diameter is taken in the wet stage. This can also be assessed in this preparatory test, with monitoring of the respective dimensions. If these change such that either a gap is formed, or the sample forms wrinkles which would prevent it from smoothly contacting the porous screens or frits, the cut diameter should be adjusted accordingly.

The test sample (19110) is placed inside the hole in the gasket foam (19115), and the composite is placed on top of the bottom half of the sample cell, ensuring that the sample is in flat, smooth contact with the screen (19135), and no gaps are formed at the sides.

The top of the test cell (19121) is laid flat on the lab bench (or another horizontal plane) and all three caliper gauges (19145) mounted thereon are zeroed.

The top of the test cell (19121) is then placed onto the bottom part (19122) such that the gasket material (19115) with the test sample (19110) lays in between the two parts. The top and bottom part are then tightened by the fixation screws (19140), such that the three caliper gauges are adjusted to the same value as measured for the wet sample under the respective pressure in the above.

2) To prepare the experiment, the program on the computerized unit (19190) is started and sample identification, respective pressure etc. are entered.
3) The test will be run on one sample (19110) for several pressure cycles, with the first pressure being the lowest pressure. The results of the individual pressure runs are put on different result files by the computerized unit (19190). Data are taken from each of these files for the calculations as described below. (A different sample should be used for any subsequent runs of the material.)
4) The inlet liquid reservoir (19150) is set to the required height and the test is started on the computerized unit (19190).
5) Then, the sample cell (19120) is positioned into the permeameter unit with Quick Disconnect fittings (19189).
6) The sample cell (19120) is filled by opening the vent valve (19188) and the bottom fill valves (19184, 19186). During this step, care must be taken to remove air bubbles from the system, which can be achieved by turning the sample cell vertically, forcing air bubbles—if present—to exit the permeameter through the drain. Once the sample cell is filled up to the tygon tubing attached to the top of the chamber (19121), air bubbles are removed from this tubing into the waste reservoir (19156).
7) After having carefully removed air bubbles, the bottom fill valves (19184, 19186) are closed, and the top fill (19182) valve is opened, so as to fill the upper part, also carefully removing all air bubbles.
8) The fluid reservoir is filled with test fluid to the fill line (19152).

Then the flow is started through the sample by initiating the computerized unit (19190).

After the temperature in the sample chamber has reached the required value, the experiment is ready to begin.

Upon starting the experiment via the computerized unit (19190), the liquid outlet flow is automatically diverted from the waste reservoir (19156) to the outlet reservoir (19154), and pressure drop, and temperature are monitored as a function of time for several minutes.

Once the program has ended, the computerized unit provides the recorded data (in numeric and/or graphical form).

If desired, the same test sample can be used to measure the permeability at varying pressure heads, with there by increasing the pressure from run to run.

The equipment should be cleaned every two weeks, and calibrated at least once per week, especially the frits, the load cell, the thermocouple and the pressure transducer, thereby following the instructions of the equipment supplier.

The differential pressure is recorded via the differential pressure transducer connected to the pressure probes measurement points (19194, 19196) in the top and bottom part of the sample cell. Since there may be other flow resistances within the chamber adding to the pressure that is recorded, each experiment must be corrected by a blank run. A blank run should be done at 10, 20, 30, 40, 50, 60, 70, 80 cm requested pressure, each day. The permeameter will output a Mean Test Pressure for each experiment and also an average flow rate.

For each pressure that the sample has been tested at, the flow rate is recorded as Blank Corrected Pressure by the computerized unit (19190), which is further correcting the Mean Test Pressure (Actual Pressure) at each height recorded pressure differentials to result in the Corrected Pressure. This Corrected Pressure is the DP that should be used in the permeability equation below.

Permeability can then be calculated at each requested pressure and all permeabilities should be averaged to determine the k for the material being tested.

Three measurements should be taken for each sample at each head and the results averaged and the standard deviation calculated. However, the same sample should be used, permeability measured at each head, and then a new sample should be used to do the second and third replicates.

The measuring of the in-plane permeability under the same conditions as the above described transplanar permeability, can be achieved by modifying the above equipment such as schematically depicted in FIGS. 2A and 2B showing the partly exploded, not to scale view of the sample cell only. Equivalent elements are denoted equivalently, such that the sample cell of FIG. 2 is denoted (20210), correlating to the numeral (19110) of FIG. 1, and so on. Thus, the transplanar simplified sample cell (19120) of FIG. 1 is replaced by the in-plane simplified cell (20220), which is designed so that liquid can flow only in one direction (either machine direction or cross direction depending on how the sample is placed in the cell). Care should be taken to minimize channeling of liquid along the walls (wall effects), since this can erroneously give high permeability reading. The test procedure is then executed quite analogous to the transplanar test.

The sample cell (20220) is designed to be positioned into the equipment essentially as described for the sample cell (20120) in the above transplanar test, except that the filling tube is directed to the inlet connection (20232) the bottom of the cell (20220). FIG. 2A shows a partly exploded view of the sample cell, and FIG. 2B a cross-sectional view through the sample level.

The test cell (20220) is made up of two pieces: a bottom piece (20225) which is like a rectangular box with flanges, and a top piece (20223) that fits inside the bottom piece (20225) and has flanges as well. The test sample is cut to the size of 2" in ×2" in (about 5.1 cm by 5.1 cm) and is placed into the bottom piece. The top piece (20223) of the sample chamber is then placed into the bottom piece (20225) and sits on the test sample (20210). An incompressible neoprene rubber seal (20224) is attached to the upper piece (20223) to provide tight sealing. The test liquid flows from the inlet reservoir to the sample space via Tygon tubing and the inlet connection (20232) further through the outlet connection (20233) to the outlet reservoir. As in this test execution the temperature control of the fluid passing through the sample cell can be insufficient due to lower flow rates, the sample is kept at the desired test temperature by the heating device (20226), whereby thermostated water is pumped through the heating chamber (20227). The gap in the test cell is set at the caliper corresponding to the desired wet compression, normally 0.2 psi (about 1.4 kPa). Shims (20216) ranging in size from 0.1 mm to 20.0 mm are used to set the correct caliper, optionally using combinations of several shims.

At the start of the experiment, the test cell (20220) is rotated 900 (sample is vertical) and the test liquid allowed to enter slowly from the bottom. This is necessary to ensure that all the air is driven out from the sample and the inlet/outlet connections (20232/20233). Next, the test cell (20220) is rotated back to its original position so as to make the sample (20210) horizontal. The subsequent procedure is the same as that described earlier for transplanar permeability, i.e. the inlet reservoir is placed at the desired height, the flow is allowed to equilibrate, and flow rate and pressure drop are measured. Permeability is calculated using Darcy's law. This procedure is repeated for higher pressures as well.

For samples that have very low permeability, it may be necessary to increase the driving pressure, such as by extending the height or by applying additional air pressure on the reservoir in order to get a measurable flow rate. In plane permeability can be measured independently in the machine and cross directions, depending on how the sample is placed in the test cell.

What is claimed is:

1. A liquid handling member for absorbing body liquids wherein said liquid handling member has a capillary sorption absorption height at 50% of its capacity at 0 cm absorption height (CSAH50) of at least 50 cm and in that said liquid handling member has a liquid permeability of at least 5 Darcy.

2. A liquid handling member according to claim 1, wherein said liquid handling member has a liquid permeability of at least 10 Darcy.

3. A liquid handling member for absorbing body liquids wherein said liquid handling member has a capillary sorption absorption height at 50% of its capacity at 0 cm absorption height (CSAH50) of at least 80 cm and in that said liquid handling member has a liquid permeability of at least 2 Darcy.

4. A liquid handling member for absorbing body liquids wherein said liquid handling member has a capillary sorption absorption height at 50% of its capacity at 0 cm absorption height (CSAH50) of at least 80 cm and in that said liquid handling member has an absorption time to 80% of its capacity of less than 5 seconds.

5. A liquid handling member according to claim 1 further having a capillary sorption absorption capacity at 100 cm absorption height of at least 5 g/g.

6. A device for handling body liquids comprising a liquid handling member according to claim 1.

7. An absorbent structures comprising a first region for acquisition/distribution of fluid, said first region comprising at least one member for acquiring and/or transporting liquid and a second region for storage of fluid, said second region comprising a liquid handling member wherein said liquid handling member has a capillary sorption absorption height at 50% of its capacity at 0 cm absorption height (CSAH50) of at least 50 cm and in that said liquid handling member has a liquid permeability of at least 5 Darcy.

8. A device for handling body liquids comprising an absorbent structure according to claim 7.

9. A device for handling body liquids according to claim 6, wherein said device is a disposable absorbent article.

10. A device for handling body liquids according to claim 9, wherein said device is a disposable diaper.

* * * * *

UNITED STATES PATENT AND TRADEMARK OFFICE
CERTIFICATE OF CORRECTION

PATENT NO. : 6,506,960 B1
DATED : January 14, 2003
INVENTOR(S) : Young et al.

It is certified that error appears in the above-identified patent and that said Letters Patent is hereby corrected as shown below:

Column 2,
Line 50, delete "Attentively" and insert -- Alternatively --.

Column 4,
Line 63, delete "of-the" and insert -- of the --.

Column 5,
Line 14, delete "Ehmsperger" and insert -- Ehrnsperger --.

Column 9,
Line 9, delete "AS56BA" and insert -- AS568A --.

Column 11,
Line 9, delete "Somtion" and insert -- Sorption --.

Column 13,
Line 16, delete "Caipillary Sormtion" and insert -- Capillary Sorption --.
Line 60, delete "586" and insert -- 566 --.
Line 64, delete "12.5" and insert -- /2.5 --.

Column 16,
Line 3, delete "electronic-balance" and insert -- electronic balance --.

Column 17,
Line 57, delete "I9194" and insert -- 19194 --.

Column 20,
Line 8, delete "there by" and insert -- thereby --.

UNITED STATES PATENT AND TRADEMARK OFFICE
CERTIFICATE OF CORRECTION

PATENT NO.    : 6,506,960 B1
DATED         : January 14, 2003
INVENTOR(S)   : Young et al.

It is certified that error appears in the above-identified patent and that said Letters Patent is hereby corrected as shown below:

<u>Column 21</u>,
Line 19, delete "900" and insert -- 90º --.

Signed and Sealed this

Twenty-seventh Day of April, 2004

JON W. DUDAS
*Acting Director of the United States Patent and Trademark Office*